United States Patent [19]

Nelson et al.

[11] Patent Number: 4,654,341

[45] Date of Patent: Mar. 31, 1987

[54] METHOD AND TABLET FOR SANITIZING TOILETS

[75] Inventors: G. Douglas Nelson; Steve Vazopolos, both of St. Louis, Mo.

[73] Assignee: Monsanto Company, St. Louis, Mo.

[21] Appl. No.: 785,104

[22] Filed: Oct. 7, 1985

Related U.S. Application Data

[63] Continuation-in-part of Ser. No. 529,799, Sep. 6, 1983, abandoned.

[51] Int. Cl.$^4$ ............... A01N 59/08; A61J 3/10; A61K 27/12
[52] U.S. Cl. .................................................. 514/241
[58] Field of Search ............... 424/14, 149, 19; 514/241

[56] References Cited

U.S. PATENT DOCUMENTS

| | | | |
|---|---|---|---|
| 2,913,460 | 11/1959 | Brown | 424/249 |
| 3,108,078 | 10/1963 | Wixon | 424/249 |
| 3,120,378 | 2/1964 | Lee et al. | 514/241 |
| 3,293,188 | 12/1966 | Brown et al. | 514/241 |
| 3,296,069 | 1/1967 | Kowalski | 514/241 |
| 3,342,674 | 9/1967 | Kowalski | 514/241 |
| 3,454,699 | 7/1969 | Symes | 424/249 |
| 3,488,420 | 1/1970 | Keast et al. | 514/241 |
| 3,506,764 | 4/1970 | Schneider et al. | 514/241 |
| 3,554,915 | 1/1971 | Keay et al. | 514/241 |
| 3,856,932 | 12/1974 | May | 424/149 |
| 3,873,685 | 3/1975 | Kibbel | 514/241 |
| 3,956,444 | 5/1976 | Kibbel | 514/241 |
| 4,288,430 | 9/1981 | Etzel | 514/241 |
| 4,557,926 | 10/1985 | Nelson et al. | 514/241 |

FOREIGN PATENT DOCUMENTS

WO8100340  2/1981  PCT Int'l Appl. ............ 514/241

OTHER PUBLICATIONS

Ruck CA. 90 #8026S (1979) of U.S. Pat. No. 4,116,850.
Amanrica CA. 88#52305G (1978) of Ger. Off. 2713364.

Primary Examiner—Shep K. Rose
Attorney, Agent, or Firm—Thomas E. Kelley; Wendell W. Brooks; Arthur E. Hoffman

[57] ABSTRACT

Disclosed is a tablet suitable for disinfecting a flush toilet comprising an alkali metal salt of dichloroisocyanuric acid and either calcium chloride or barium chloride, in which the mole ratio of the alkali metal salt of dichloroisocyanuric acid to chloride salt is no greater than 4:1. Also disclosed is a method of using the tablet.

15 Claims, No Drawings

METHOD AND TABLET FOR SANITIZING TOILETS

This is a continuation-in-part, of application Ser. No. 529,799, filed Sept. 6, 1983, now abandoned.

FIELD OF THE INVENTION

This invention relates to sanitizing and disinfecting flush toilets. More particularly, this invention relates to automatic toilet bowl cleaners.

BACKGROUND

A number of different compositions and methods for disinfecting flush toilets have been proposed. These include various hypochlorite and chloramine compounds, that can be dispensed from a single-compartment dispenser, such as is described in U.S. Pat. No. 4,318,891, or from a two-compartment dispenser such as is described in U.S. Pat. Nos. 3,618,143 or 4,208,746. The disinfecting composition can be employed as granules, but is more commonly employed as a tablet.

In order to act effectively in automatic toilet bowl cleaners, the disinfectant tablet must have a number of properties. The tablet should have a useful life approaching 300 flushes, and should produce a disinfectant concentration from about 2 to about 30 parts per million, preferably from about 5 to about 20 parts per million, per flush. The tablet must not produce objectionable chloramine or other objectionable odors. The tablets must retain their integrity throughout the useful life of the toilet bowl cleaner and must not crumble or disintegrate so as to plug the various holes and passages in the dispenser, through which water is circulated as the toilet tank fills and drains. The disinfectant tablet must not cause corrosion of the metal parts of the toilet or other adverse effects on other portions of the fixtures. The tablet must not appreciable contribute to formation of scale or other insolubles or contain insoluble components. Additionally, the tablet must not contribute toxic substances to the sewage system, the water supply, or the environment.

The most commonly used disinfectant tablet materials are calcium hypochlorite and trichloroisocyanuric acid. Each of these substances has major drawbacks. Calcium hypochlorite contains insoluble components that can plug the holes in the dispenser, and also contributes to water hardness and scale formation by adding calcium ions to the water. Trichloroisocyanuric acid is a strong acid and can produce objectionable chloramine odors under some circumstances.

A disinfectant tablet that produces an appropriate concentration of disinfectant, with the requisite lifetime and tablet integrity, and without the negative properties discussed above would be an advancement in the art.

SUMMARY OF THE INVENTION

This invention provides a tablet suitable for disinfecting a flush toilet, comprising an alkali metal salt of dichloroisocyanuric acid, preferably sodium dichloroisocyanuric acid dihydrate, and a chloride salt selected from the group consisting of calcium chloride and barium chloride, preferably calcium chloride dihydrate and barium chloride dihydrate, in which the molar ratio of alkali metal dichloroisocyanuric acid to chloride salt is no greater than 4:1, preferably no greater than 3:1, and most preferably substantially stoichiometric. The tablet preferably contains at least about 40% alkali metal dichloroisocyanuric acid more, preferably at least about 50%, and most preferably at least about 60%. The Tablet is essentially free of sodium carbonate/bicarbonate buffer mixtures, and it is capable of prolonged rlease of chlorine through metered dispensers when immersed in water. The tablet also preferably contains a mold release agent, such as boric acid or monoglyceryl stearate. This invention also provides a method for disinfecting a flush toilet comprising contacting a tablet as described above with the water provided to flush the toilet, particularly where the water provided to flush the toilet is contained in a tank that is part of the toilet.

DESCRIPTION OF THE INVENTION

The use of alkali metal salts of dichloroisocyanuric acid in tabletted toilet bowl disinfects has a major drawback in that their solubility in water is large enough so that the tablets do not have sufficient lifetime. The tablets of this invention reduce the solubility of the alkali metal salt of dichloroisocyanuric acid by providing barium and calcium ions that can react with the dichloroisocyanuric acid to form either barium di(dichloroisocyanuric acid) or calcium di(dichloroisocyanuric acid). These divalent metal salts are less soluble than the alkali metal salts, and the tablet exhibits this lower solubility. In short, the tablet behaves as though it were made, at least in part, of barium di(dichloroisocyanuric acid) or calcium di(dichloroisocyanuric acid), instead of the more common, and less costly, alkali metal salts of dichloroisocyanuric acid.

In theory, this same approach ought to work with a variety of divalent metal salts. However, the formulation must be tablettable in order to be useful with the dispensers that are commonly used with toilet bowl cleaners. The dispenser normally includes a container for the disinfectant tablet with openings or passages through which water flows during the flushing cycle. In this way, the tablet becomes partially or fully immersed in water, and dissolves to release the disinfectant. This solution is dispensed to the toilet during flushing. This type of dispenser is disclosed in U.S. Pat. No. 3,618,143 and U.S. Pat. No. 4,208,747, which are incorporated herein by reference. In this type of dispenser, and other dispensing systems, it is necessary that the tablet maintain its integrity, so that water can flow around the tablet to get the appropriate dissolution of disinfectant, and so that the openings and passages do not get clogged. The formulations of this invention form tablets that do not disintegrate in water as do many other formulations containing other divalent metal compounds. This tablet integrity is central to the operation of this invention.

The tablets of this invention are particularly suited to use in dispensers of the type discussed above, but can also be used with other disinfecting systems where tablet integrity is either necessary or desirable, such as "under the rim" toilet bowl cleaners, in which flushing water washes over a tablet hung under the toilet bowl rim.

The alkali metal salt of dichloroisocyanuric acid that can be used with this invention can be either potassium or sodium, with sodium being preferred. It is also preferred that the alkali metal salt of dichloroisocyanuric acid be fully hyrated. Sodium dichloroisocyanuric acid dihydrate is the most preferred species. It is preferred that the tablet be at least about 40% by weight, more preferably at least about 50% and most preferably at least about 60% by weight alkali metal salt of dichloroisocyanuric acid.

In order for the tablets of this invention to function, there must be sufficient barium chloride or calcium chloride to convert a substantial portion of the alkali metal salt to the calcium or barium salt. Good results are obtained when the mole ratio of dichloroisocyanuric acid to barium or calcium is no greater than 4:1, preferably no greater than 3:1, most preferably no greater than 2:1 (which is the stoichiometric amount). It is also possible to use an excess of barium chloride or calcium chloride.

In addition to the ingredients discussed above, the tablets may also contain additional ingredients. Trichloroisocyanuric acid may be added to increase the amount of available chlorine in the formulation. "Available chlorine" is commonly used term which means the amount of active chlorine by weight in a composition compared with the amount of active chlorine by weight in chlorine gas, expressed as a percent. If the amount of trichloroisocyanuric acid in the composition is too large, objectionable chloramine odors can be produced. The tablets may contain tabletting aids, such as lubricants, mold release agents, binders, etc. The most commonly used mold release agents are boric acid and monoglyceryl stearate. It is preferred tha the formulation contain about 2% mold release agent. The formulation may also include a filler, such as sodium chloride. The filler can act to reduce solubility, assist in tabletting, or perform other functions.

It is preferred that all of the components of the formulation be fully hydrated, so that hydration does not occur after tabletting, which can be harmful to tablet integrity.

The tablet of this invention can either be used alone, to provide disinfection of the toilet bowl, or, preferably, in combination with another tablet that provides a detergent or surfactant, a perfume, a dye, and the like, to provide more complete toilet bowl cleaning.

The following Examples are intended to illustrate this invention, and are not intended in any limiting sense. In the Examples, as well as in the discussion above, all parts and percentages are by weight, unless otherwise specified.

EXAMPLES 1-8

Tablets were prepared with 1.75 inch (3.8 cm.) diameter on a press at 9100-9800 psi (62,700-67,500 kPa) of pressure. The tablets contained 33 g with the compositions indicated. Sodium dichloroisocyanuric acid dihydrate ($NaCl_2 2CYA.2H_2O$) was used as the alkali metal dichloroisocyanuric acid. Additionally, each tablet contained 1% $H_3BO_3$ and 0.5% monoglyceryl stearate, to act as mold release agents. The tablets were placed in a dispenser similar to that described in U.S. Pat. No. 4,208,747, and the dispenser was placed in a container of water. To simulate flushing of a toilet, the dispenser periodically was raised out of the water and allowed to drain. The amount of active chlorine dispensed was determined amperometrically, and the concentration, in parts per million released to a toilet was estimated and reported as "ppm Chlorine". The lifetime, in days, was also estimated. Many tablets swelled and disintegrated, so these data were not available.

TABLE I

| Example Number | Composition | ppm Chlorine | Est. Lifetime (Days) |
|---|---|---|---|
| 1. | 66% $NaCl_2CYA.2H_2O$ 33% $BaCl_2.2H_2O$ | 3-4 | 30 |
| 2. | 74% $NaCl_2CYA.2H_2O$ 25% $BaCl_2.2H_2O$ | 19-24 | 30 |
| 3. | 74% $NaCl_2CYA.2H_2O$ 25% $CaCl_2.2H_2O$ | 4-20 | 14 |
| 4. | 74% $Na_1Cl_2CYA.2H_2O$ 25% $CaCO_3$ | tablet disintegrated | |
| 5. | 74% $NaCl_2CYA.2H_2O$ 25% $MgCl_2.6H_2O$ | tablet disintegrated | |
| 6. | 66% $NaCl_2CYA.2H_2O$ 26% $MgCl_2.6H_2O$ 7% NaCl | tablet disintegrated | |
| 7. | 74% $NaCl_2CYA.2H_2O$ 25% $SrCl_2.2H_2O$ | tablet disintegrated | |
| 8. | 74% $NaCl_2CYA.2H_2O$ 25% $Zn(C_2H_3O_2)_2.2H_2O$ | tablet disintegrated | |

As can be seen from the data of table I, mixtures of alkali metal dichloroisocyanuric acid and divalent metal compounds are very difficult to tablet. The only compounds with which tablets could successfully be made are barium chloride and calcium chloride.

EXAMPLES 9-12

Tablets were made in similar manner, with similar diameter to those in Examples 1-8, except that 50 g of the composition was used. Tablets were prepared using barium chloride and calcium chloride, and sodium dichloroisocyanuric acid at the indicated percentages along with 1% $H_3BO_3$ and 1% monoglyceryl stearate. The tables were placed in a dispenser similar to that used in Examples 1-8, which was placed in the tank of a standard flush toilet, adapted to flush automatically approximately hourly. Samples of the water were taken periodically and were analyzed as in Example 1-8 for chlorine concentration in parts per million reported as "ppm Chlorine", and the lifetime of the tablets was determined, assuming approximately 10 fushes per day. The results, along with the mole ratio of $NaCl_2CYA.2H_2O$ to barium or calcium, are shown in Table II.

TABLE II

| Ex. No. | Composition | Mole Ratio | ppm Chlorine | lifetime (days) |
|---|---|---|---|---|
| 9. | 74% $NaCl_2CYA.2H_2O$ 24% $BaCl_2.2H_2O$ | 2.94 | 3-20 | ~30 |
| 10. | 66% $NaCl_2CYA.2H_2O$ 24% $BaCl_2.2H_2O$ | 1.98 | 3-6 | ~20 |
| 11. | 74% $NaCl_2CYA.2H_2O$ 24% $CaCl_2.2H_2O$ | 1.77 | 6-34 | 8 |
| 12. | 76% $NaCl_2CYA.2H_2O$ 22% $CaCl_2.2H_2O$ | 1.98 | — | 2 |

Each of the tablets maintained its integrity throughout the test. The lifetime of the tablets, particularly those using calcium chloride was shorter than the 30 days sought for most commercial toilet bowl cleaners. This could be remedied by increasing the size of the tablet, adding a filler to decrease solubility of the tablet, or both. By making these fairly minor adjustments, a toilet bowl formulation could be made to take advantage of the good tabletting characteristics of these formulations.

We claim:

1. A tablet suitable for disinfecting a flush toilet, comprising an alkali metal salt of dichloroisocyanuric acid and a chloride salt selected from calcium chloride and barium chloride, where the molar ratio of alkali metal dichloroisocyanuric acid to chloride salt is no greater than 4:1, said tablet being essentially free of sodium carbonate/bicarbonate buffer mixtures, and capable of prolonged release of chlorine through metered dispensers when immersed in water.

2. The tablet of claim 1 wherein the alkali metal salt of dichloroisocyanuric acid is sodium dichloroisocyanuric acid dihydrate.

3. The tablet of claim 2, in which the chloride salt is calcium chloride dihydrate.

4. The tablet of claim 2 in which the chloride salt is barium chloride dihydrate.

5. The tablet of claim 1, further comprising a mold release agent selected from the group consisting of boric acid and monoglyceryl stearate. a mold release agent.

6. The tablet of claim 1 wherein the chloride salt is calcium chloride.

7. The tablet of claim 1 wherein the chloride salt is barium chloride.

8. The tablet of claim 1, wherein the mole ratio of alkali metal dichloroisocyanuric acid to chloride salt is no greater than 3:1.

9. The table of claim 1 wherein the mole ratio of alkali metal dichloroisocyanuric acid to chloride salt is about 1:2.

10. A tablet suitable for disinfecting a flush toilet, comprising at least about 40% by weight of sodium dichloroisocyanuric acid dihydrate, a chloride salt selected from the group consisting of barium chloride dihydrate and calcium chloride dihydrate, and one or more mold release agents, in which the mole ratio of sodium dichloroisocyanuric acid to chloride salt is no greater than 3:1, said tablet being essentially free of sodium carbonate/bicarbonate buffer mixtures, and capable of prolonged release of chlorine through metered dispensers when immersed in water.

11. The tablet of claim 10 in which the mole ratio of sodium dichloroisocyanuric acid to chloride salt is about 1:2.

12. A method for disinfecting a flush toilet, comprising placing the tablet of claim 1 in contact with water provided to flush the toilet.

13. The method of claim 12 wherein the water provided to flush the toilet is contained in a tank.

14. A method for disinfecting a flush toilet, comprising placing the tablet of claim 10 in contact with water provided to flush the toilet.

15. The method of claim 14 wherein the water provided to flush the toilet is contained in a tank.

* * * * *